(12) United States Patent
Rohde et al.

(10) Patent No.: US 12,023,427 B2
(45) Date of Patent: Jul. 2, 2024

(54) SYSTEM AND METHOD TO EFFICIENTLY CLEAN A BLOOD FILTER

(71) Applicants: Baxter International Inc., Deerfield, IL (US); Baxter Healthcare SA, Glattpark (CH)

(72) Inventors: Justin Rohde, Des Plaines, IL (US); Derek Wiebenson, Zurich (CH)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 34 days.

(21) Appl. No.: 17/892,395

(22) Filed: Aug. 22, 2022

(65) Prior Publication Data

US 2022/0395617 A1 Dec. 15, 2022

Related U.S. Application Data

(63) Continuation of application No. 16/673,317, filed on Nov. 4, 2019, now Pat. No. 11,419,967, which is a continuation of application No. 15/980,387, filed on May 15, 2018, now Pat. No. 10,463,775, which is a continuation of application No. 13/736,602, filed on Jan. 8, 2013, now Pat. No. 9,968,723.

(51) Int. Cl.
*A61M 1/16* (2006.01)

(52) U.S. Cl.
CPC .......... *A61M 1/168* (2013.01); *A61M 1/1682* (2014.02); *A61M 1/1686* (2013.01); *A61M 1/1688* (2014.02); *A61M 1/169* (2013.01)

(58) Field of Classification Search
CPC .. A61M 1/168; A61M 1/1682; A61M 1/1686; A61M 1/1688; A61M 1/169; B01D 2321/02; B01D 2321/04; B01D 2321/18; B01D 2321/2066; B01D 2321/2083; B01D 2321/40; B01D 65/02; B01D 65/022
See application file for complete search history.

*Primary Examiner* — Dirk R Bass
(74) *Attorney, Agent, or Firm* — K&L Gates LLP

(57) ABSTRACT

A peritoneal dialysis apparatus includes a filter and a dialysis fluid circuit in fluid communication with the filter. The peritoneal dialysis apparatus also includes a pump for pumping fresh dialysis fluid to a peritoneum of a patient via the dialysis fluid circuit and pumping used dialysis fluid from the peritoneum of the patient through the dialysis fluid circuit and the filter. The peritoneal dialysis apparatus further includes a selective air access in fluid communication with the dialysis fluid circuit and a control unit configured to control the pump during a peritoneal dialysis treatment and a filter cleaning sequence. The control unit forms a fluid mixture during a filter cleaning sequence by opening the selective air access to mix air with a physiologically safe fluid. The fluid mixture is transferred across insides and/or outsides of the filter at least one time.

22 Claims, 2 Drawing Sheets

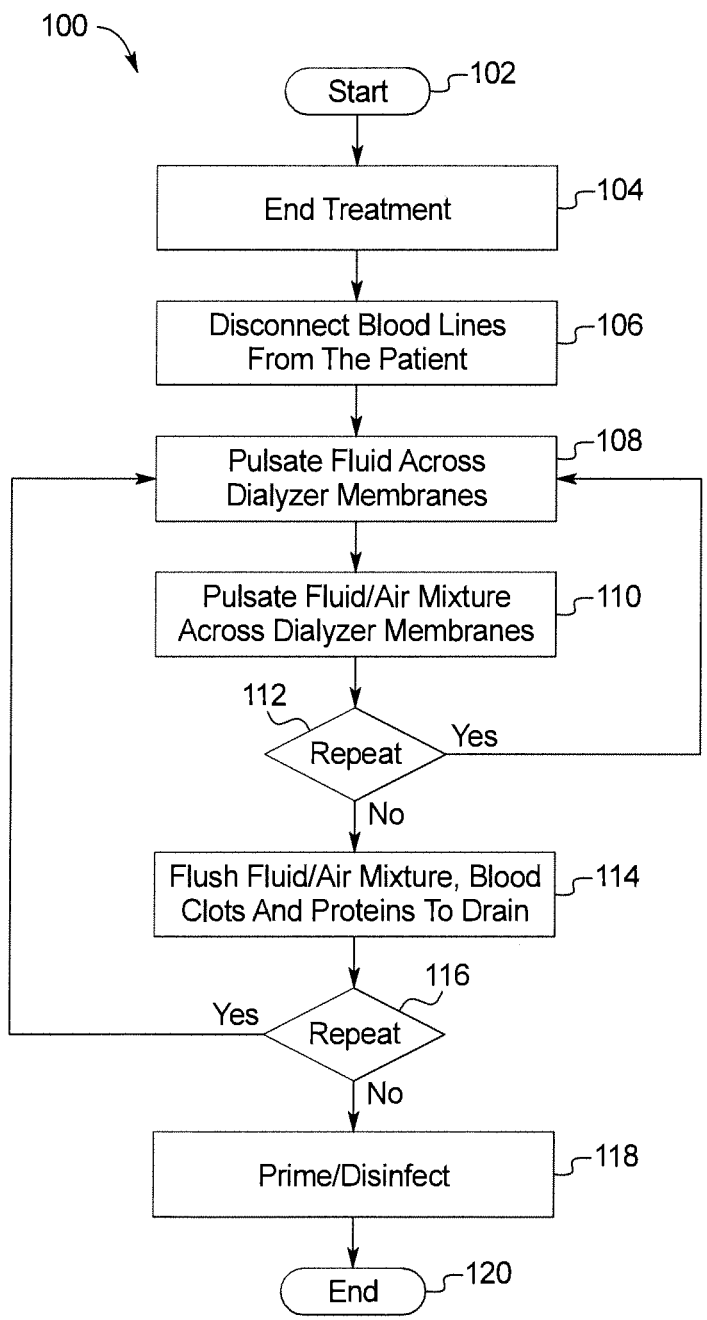

SYSTEM AND METHOD TO EFFICIENTLY CLEAN A BLOOD FILTER

PRIORITY CLAIM

This application claims priority to and the benefit as a continuation application of U.S. patent application Ser. No. 16/673,317, filed Nov. 4, 2019, entitled "System and Method to Efficiently Clean a Blood Filter", now U.S. Pat. No. 11,419,967, which is a continuation of U.S. patent application Ser. No. 15/980,387, filed May 15, 2018, entitled "System and Method to Efficiently Clean a Blood Filter", now U.S. Pat. No. 10,463,775, which is a continuation of U.S. patent application Ser. No. 13/736,602, filed Jan. 8, 2013, entitled "System and Method to Efficiently Clean a Blood Filter", now U.S. Pat. No. 9,968,723, the entire contents of which are incorporated herein by reference and relied upon.

BACKGROUND

The examples discussed below relate generally to medical fluid delivery. More particularly, the examples relate to systems, methods and apparatuses for the cleaning of blood filters, such as dialyzers or hemofilters.

Many current dialyzers are not reused, they are instead discarded after a single use. In the event that dialyzers are reused, they are most often flushed with copious amounts of water, and/or very strong chemicals to remove residual biological fluids and disinfect the membrane. Dialyzers can alternatively be disinfected with heat, eliminating the need for chemicals but still requiring water. Dialysis systems also require that excess biological residuals be removed from the dialyzer periodically. For ecological and cost reasons, and especially for systems used in the home and for travel, it is desirable to minimize the amount of water used for such cleaning and disinfecting.

An improved blood filter cleaning and disinfecting system and method are needed accordingly.

SUMMARY

By recirculating fluid in a blood filter, and by injecting air bubbles into the circuit at opportune times, the efficiency of the cleaning procedure for the blood filter can be maximized without consuming vast quantities of water.

The examples below describe systems and methods that provide a blood treatment for a patient. The blood treatment can be any blood filtering treatment, such as hemodialysis ("HD"), hemofiltration ("HF"), hemodiafiltration ("HDF"), or continuous renal replacement therapy ("CRRT"). A common thread between these treatments is that an associated filter, e.g., hemodialyzer or hemofilter, can be reused. If not reused, the filter is discarded. If reused, the filter needs to be cleaned on a periodic basis, e.g., between each use. In one embodiment, the system and method of the present disclosure clean the filter after each treatment, just prior to a disinfection sequence in which the treatment fluid lines and blood lines are cleaned either with hot water or a chemical disinfectant. It is contemplated to perform the filter cleaning process of the present disclosure after treatment when the blood lines have been disconnected from the patient and connected together either directly or via a treatment fluid loop.

One goal of the present disclosure is to clean or rinse the dialyzer without using a large amount of fluid, such as dialysate, replacement fluid or saline. Another goal of the present disclosure is to clean or rinse the blood filter effectively. In the system and method described herein, a volume on the order of 250 ml of dialysate, saline or replacement fluid may be used to clean the dialyzer. As described in detail below, the dialysate, saline or replacement fluid is reversed back and forth, or pulsed, through the blood filter and combined at opportune times with air to effectively remove blood clots, proteins, residual biological fluids and the like from the filter membranes to clean the filter for future use.

As mentioned above, regardless of the type of machine or therapy employed, a filter is provided. The filter is connected fluidly to a blood pump so that the blood pump can pump blood through the insides of the filter membranes to clean the blood. At least one treatment fluid pump is provided to pump treatment fluid, e.g., dialysate for HD, HDF and CRRT or replacement fluid for HF, HDF and CRRT, to clean the blood and to remove used treatment fluid from the filter. With HD, for example, a first treatment fluid pump pumps dialysate to the dialyzer, while a second treatment fluid pump removes used dialysate from the dialyzer. With HF, a first replacement fluid pump pumps replacement fluid directly to the blood tubing connected to a hemofilter, while a second pump removes used replacement fluid from the hemofilter. With HDF, the HD configuration is combined with a third pump that pumps replacement fluid directly to the blood tubing connected to the hemodialyzer. CRRT can have any of the pumping configurations and perform any of HD, HF or HDF and in general is a slowed or low flowrate version of the corresponding HD, HF or HDF therapy. CRRT is performed in a hospital setting and typically for acute kidney failure.

Another component of the present disclosure that is provided regardless of the type of machine or therapy employed is an access to ambient air. The air in one embodiment is introduced on the blood side of the filter so that the air can travel to the blood sides or insides of the filter membranes. The air can be introduced through an air filter that removes contaminants from the air and cleans the air so as to be suitable for injecting into the blood circuit, even though the air is eventually purged from the entire system, and the circuit is disinfected.

The blood and treatment pumps may be of a type suitable for medical fluid delivery and are typically peristaltic or volumetric type membrane or diaphragm pumps. The pumps may operate with one or more valve that selectively opens and closes a line or tube leading to and/or from each pump. Each of the pumps and valves is controlled automatically by a control unit or controller that uses one or more processor and memory. The pumps and valves may be operated pneumatically, electromechanically or via some combination thereof. In one embodiment, the controller or control unit operates the pumps and valves according to the following sequence to clean or rinse the dialyzer.

In a first phase of the sequence, the system and method of the present disclosure attempt to loosen blood clots, proteins and biological fluids from the insides of the filter membranes by reversing treatment fluid back and forth (pulsating the fluid) across the insides and/or outsides of the filter membranes. The reversing of the treatment fluid can be done via the blood pump, a treatment fluid pump, or both. In this manner, the insides and/or outsides of the membrane walls are fluidly scrubbed. And because the same fluid is moved back and forth to suspend debris within the fluid, and not sent to drain, a relatively small amount of fluid is actually needed to perform this first phase. The treatment fluid that is used can be (i) fresh fluid that has not been used in the treatment, (ii) leftover treatment fluid pulled from the treatment fluid circuit or (iii) leftover treatment fluid that has been used to rinseback blood to the patient at the end of treatment.

The cleaning fluid is in one embodiment a physiologically safe fluid, such as dialysate, replacement fluid or saline. Thus while water could be used instead of a physiologically compatible treatment fluid in this first phase, a physiologically compatible fluid is desired because it is thought that pure water would tend to create more new blood clots than the physiologically safe fluid. Alternatively, e.g., if the machine is disinfected after the dialyzer cleaning procedure of the present disclosure, the cleaning fluid can be a stronger fluid, such as a stronger acid, a stronger base, or enzymatic cleaner, which are good clot removers.

In a second phase, air is injected into the blood filter from an air access, optionally protected by an air filter. The air is pulled into the treatment fluid creating an air/treatment fluid mixture, which has a different consistency and thus scrubbing capability than pure treatment fluid. The air/treatment fluid mixture is pumped from the bottom of the filter to the top of the filter at least one time. If the air access is arranged such that air must enter the filter from its top, then the system and method of the present disclosure first pushes the air/treatment fluid mixture to the bottom or past the bottom of the filter, and then reverses pumping so as to move the air/treatment fluid mixture up from the bottom of the filter, through the filter. Doing so creates microbubbles (or effervescence) that helps to further remove blood from the dialyzer. As the microbubbles move through the small diameter of the filter fibers, the bubbles expose blood particles to alternating phases of liquid and gas, as well as a high shear stress and turbulence at the boundary layer between the two phases, causing enhanced removal from the filter wall.

In a third phase, the system and method of the present disclosure perform a depriming procedure by pulling more air in from the filtered air access. Doing so pushes the air/treatment fluid mixture, now filled with suspended blood particles including blood clots and proteins, to drain. It should be appreciated that in one embodiment, it is not until this third phase that any fluid is discarded from the system. In various embodiment, phases two, three, and four can be successively repeated to achieve better cleaning, e.g., at the cost of higher water consumption.

In a fourth phase, the blood and treatment fluid circuits are primed, e.g., with purified water or other fluid not contaminated with blood particles from the previous step. The priming removes any of the treatment fluid or air/treatment fluid mixture remaining in either circuit, sending same to drain. Once primed with water, it is contemplated for the system to run a hot water or chemical disinfection sequence. The disinfection sequence cleans the entire system including the treatment fluid lines, the blood lines and the filter. The disinfection fluid or water may then be discarded and replaced with filtered air, leaving the machine disinfected, dry and ready to perform another treatment.

While the present disclosure is described primarily in connection with a dialysis machine that reuses the same dialyzer over multiple treatments, e.g., around thirty treatments, the concepts discussed herein are not limited to such an application. For example, the apparatus and methodology could be used on a dialyzer cleaning machine. Here, the dialyzer is removed from the dialysis machine after treatment, brought to the dialyzer cleaning machine, which uses the structure and methodology discussed herein to clean the dialyzer, which is then brought back to the dialysis machine for reuse.

Further, while the present disclosure is described primarily in connection with a hemodialysis or blood machine, the present disclosure is equally applicable to a dialysis machine that uses a filter to clean a peritoneal dialysis fluid or ("PD") solution. In such case, the blood circuit below is replaced with a peritoneal dialysis circuit that pumps PD solution into and out of the patient's peritoneum.

It is therefore an advantage of the present disclosure to provide an improved renal failure therapy system and method.

Another advantage of the present disclosure is to provide an improved blood filter cleaning system and method.

A further advantage of the present disclosure to provide an improved blood filter cleaning system and method that does not require a large amount of fluid to clean the blood filter.

It is still another advantage of the present disclosure to provide an effective blood filter cleaning system and method.

Additional features and advantages are described herein, and will be apparent from, the following Detailed Description and the figures.

BRIEF DESCRIPTION OF THE FIGURES

FIG. 2 is a process flow diagram illustrating one method for cleaning a filter of the present disclosure.

DETAILED DESCRIPTION

HD/HF/HDF/CRRT/PD Systems and Methods

Figure 1:
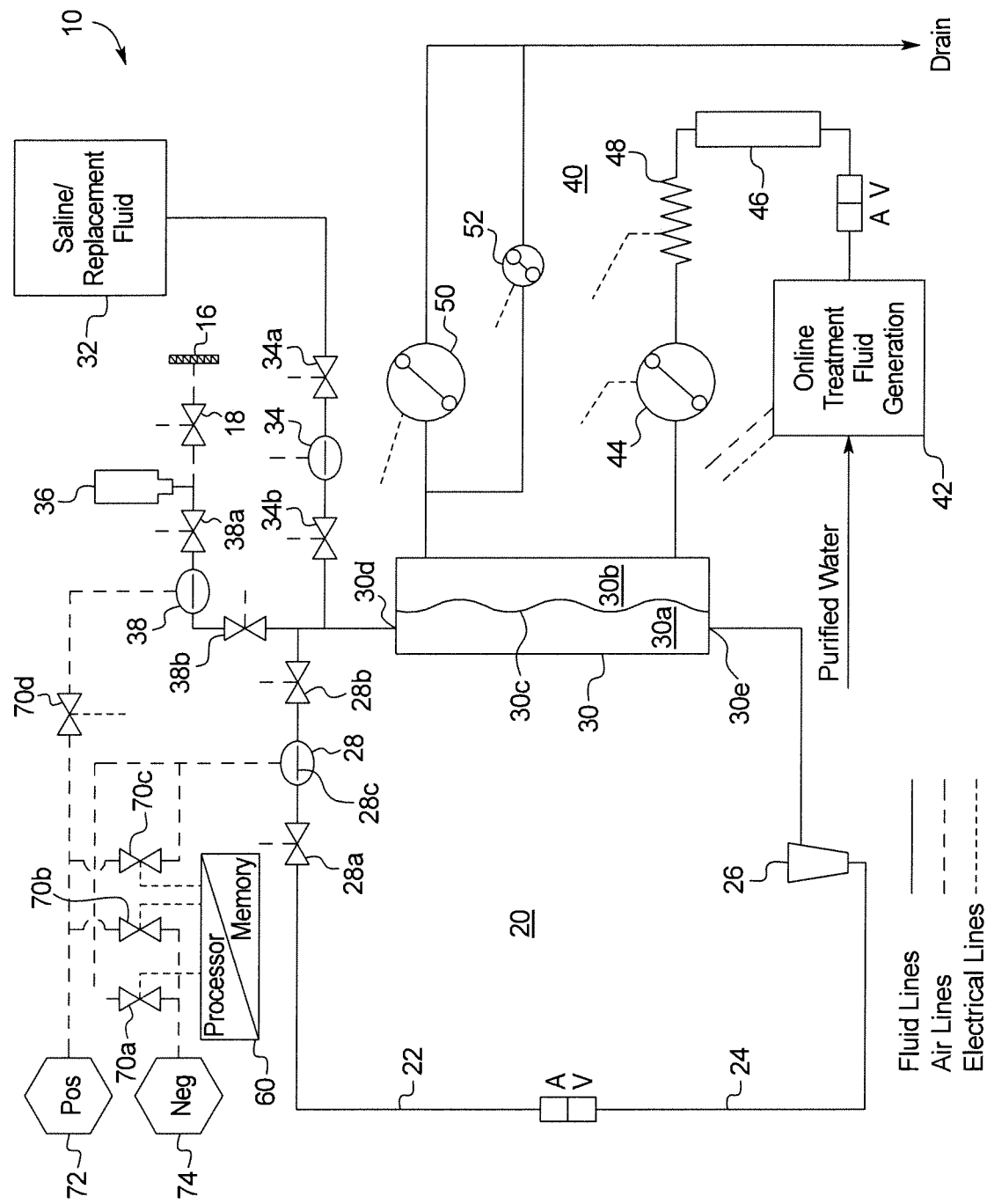
FIG. 1 is schematic illustration of one system configured and arranged to perform a filter cleaning procedure of the present disclosure.

Referring now to the drawings and in particular to FIG. 1, one embodiment for a system and method of the present disclosure is illustrated by system 10. System 10 includes a blood circuit 20 and a treatment fluid circuit 40. Blood circuit 20 includes an arterial line 22 and a venous line 24. Arterial line 22 ends with an arterial needle connector A. Venous line 24 ends with a venous needle connector V. During treatment, arterial needle connector A connects to an arterial needle or other access (e.g. a catheter), which is inserted into the patient for treatment. Venous needle connector V connects to a venous needle or other access (e.g. a catheter), which is inserted into the patient for treatment. After treatment, the arterial needle connector A can be connected to the venous needle connector V, as illustrated in FIG. 1, for the cleaning process described below. Alternatively, the arterial needle connector A and the venous needle connector V can be plugged into the treatment fluid circuit 40 at mating connectors marked A and V, respectively, after treatment for the cleaning process described below.

Venous line 24 includes a bubble trap or air trap that removes air from the blood before being returned to the patient via the venous line. Arterial line 22 includes a blood pump 28 in the illustrated embodiment. Blood pump 28 can be a peristaltic, electrically driven blood pump. In the illustrated embodiment, however, blood pump 28 is a volumetric or diaphragm type pump that operates with an upstream valve 28a and a downstream valve 28b. During operation, upstream valve 28a is opened, downstream valve 28b is closed, while pump diaphragm 28c is retracted to pull blood or other fluid into blood pump 28. In the next stroke, upstream valve 28a is closed, downstream valve 28b is opened, while pump diaphragm 28c is pushed out to likewise push blood or other fluid from blood pump 28.

Blood pump 28 pushes blood through a blood filter 30, such as a dialyzer for hemodialysis ("HD") of hemodiafiltration ("HDF"), or a hemofilter for hemofiltration ("HF"). Any of HD, HDF, and HF may be performed for continuous renal replacement therapy ("CRRT"). Filter 30 as mentioned above may also be a filter used for filtered peritoneal dialysis ("PD"). In any case, blood filter 30 has a blood side 30a and treatment fluid side 30b separated by a plurality of hollow fiber membranes 30c (modeled as a single line in FIG. 1). The insides of the hollow fiber membranes 30c form the blood side 30a, while the treatment fluid side 30b of blood filter 30 is formed between the outsides of hollow fiber membranes 30c and the inner surface of the housing of blood filter 30. In the illustrated embodiment, blood or other fluid flows into blood filter 30 at its top end 30d, through blood side 30a, and out of blood filter 30 at its bottom end 30e. The arterial and venous lines 22 and 24 can be reversed alternatively, such that blood flow during treatment flows from bottom end 30e of blood filter 30, through the filter, and out its top end 30d.

A saline and/or a replacement fluid source 32 may be provided. Replacement fluid is provided if HDF or HF is performed during treatment. Replacement fluid is an injectable quality, physiologically compatible fluid that is introduced directly into blood circuit 20, here illustrated at arterial line 22, but alternatively or additionally injected at venous line 24. Saline is used in many dialysis systems for priming. In the illustrated embodiment, a replacement fluid and/or saline pump 34 pumps replacement fluid and/or saline as needed into arterial line 22. Pump 34 can be a peristaltic pump or alternatively be a volumetric or diaphragm type pump, as is illustrated, which operates with an upstream valve 34a and a downstream valve 34b in the same manner as described above for the volumetric version of blood pump 28.

A heparin supply 36 is provided in the illustrated embodiment. A heparin pump 38 pumps heparin as needed into arterial line 22. Pump 38 can likewise be a peristaltic pump or alternatively be a volumetric or diaphragm type pump, as is illustrated, which operates with an upstream valve 38a and a downstream valve 38b in the same manner as described above for the volumetric version of blood pump 28. Heparin from supply 36 helps to prevent blood clots in blood circuit 20 and filter 30 as is known.

Treatment fluid circuit 40 makes treatment fluid, e.g., dialysate, online in one embodiment by accepting purified water from a purified water source (not illustrated). Purified water is delivered to an online treatment fluid generation unit 42 in the illustrated embodiment. Online treatment fluid generation unit 42 mixes the purified water with acid and bicarbonate concentrates to make a solution that is physiologically compatible with the patient's blood. One suitable online treatment fluid generation unit 42 is described in U.S. Patent Publication No. 2009/0008331, which published Jan. 8, 2009, entitled, "Hemodialysis Systems and Methods", the entire contents of which are incorporated herein by reference and relied upon.

A to-filter pump 44 pumps treatment fluid from online treatment fluid generation unit 42, through a pathogen filter 46, such as an ultrafilter. Pump 44 is illustrated as being a peristaltic pump but is alternatively a volumetric diaphragm pump, like pumps 28, 34 and 38. Taking purified, e.g., ultrapure water, turning it into treatment fluid or dialysate and passing the treatment fluid through an ultrafilter produces a solution at or near injectable or drug infusion quality. Pump 44 pulls the dialysate through an online heater 48 that heats the dialysate to approximately body temperature or 37° C. Heater 48 is provided for patient comfort and can be removed from treatment fluid circuit 40 if desired.

Pump 44 delivers fresh treatment fluid, e.g., dialysate, under positive pressure to treatment fluid side 30b of blood filter 30. During treatment, treatment fluid, e.g., dialysate, cleans the blood flowing (e.g., countercurrent) through the blood side 30a of blood filter 30. A from-filter pump 50 pulls spent or used dialysate from treatment fluid side 30b of blood filter 30 and delivers same to drain. Pump 50 is illustrated as being a peristaltic pump but is alternatively a volumetric diaphragm pump, as illustrated by pumps 28, 34 and 38. If provided as a volumetric diaphragm pump, it is contemplated to use pump 50 to push spent or used dialysate under positive pressure to from-filter pump 50 during its fill stroke. In this manner, treatment fluid is never under negative pressure within blood filter 30, which can cause air to come out of solution. Although not illustrate, one or more air trap can be located upstream of down stream of to-filter pump 44.

Also not illustrated, treatment fluid circuit 40 in one embodiment includes balance chambers that balance or make equal the amount of fresh treatment fluid that is delivered to blood filter 30 with spent or used fluid that is removed from blood filter 30, which prevents increasing or decreasing the amount of fluid present within the patient. The operation of the balance chambers is known to those of skill in the art but in general involves a known volume chamber that is divided by a diaphragm much like a diaphragm pump. The chamber on one side of the diaphragm receives spent treatment fluid, which moves the diaphragm to dispel a like amount of fresh treatment fluid. In a next stoke, the chamber on the other side of diaphragm receives fresh treatment fluid, which moves the diaphragm to dispel a like amount of spent treatment fluid and so on. Two balance chambers may be used out of phase with one another so that there is always some fresh fluid flow to blood filter 30 and some spent or used fluid flow from blood filter 30.

With fresh and spent treatment fluid being balanced, an ultrafiltrate ("UF") pump 52 is provided to remove a precise amount of additional fluid from the patient over the course of treatment. UF Pump 52 is illustrated as being a peristaltic pump but is alternatively a volumetric diaphragm pump, like pumps 28, 34 and 38. UF Pump 52 pulls an amount of UF off of the patient over the course of treatment in an attempt to return the patient to his or her dry weight.

A control unit 60 is provided, which can include one or more processor and one or more memory. Control unit 60 runs one or more computer program including one or more computer programs to implement method 100 illustrated in FIG. 2. The processing and memory of control unit 60 also operate with a user interface (not illustrated), which enables a user to interact with and control system 10. Control unit 60 controls via electrical signals (dotted lines) the electrically driven peristaltic pumps, such as pumps 44, 50 and 52, and heater 48. Control unit 60 can also control online treatment fluid generation unit 42 using electrical signals (dotted lines) and/or pneumatic signals (dashed lines) as illustrated. Control unit 60 also controls via electrical signals (dotted lines) each of a plurality of pneumatic valves 70a, 70b, 70c, 70d . . . 70n, which in turn control pneumatic signals (dashed lines) running to diaphragm pumps, such as pumps 28, 34 and 38 and fluid valves, such as fluid valves 28a, 28b, 34a, 34b, 38a, 38b.

One or more of pneumatic valves 70a, 70b, 70c, 70d . . . 70n also controls pneumatic signals (dashed lines) running to an air valve 18. Air valve 18 allows air filtered by a filter 16, such as a high-efficiency particulate air ("HEPA") filter, to be pumped into system 10 via heparin pump 38. It should be appreciated that while filtering the air is preferred, the air does not have to be filtered for the present disclosure, for example, if system 10 is to be disinfected. In an embodiment, negative pressure exerted on heparin vial 36 via heparin pump 38 is relieved by opening air valve 18 and allowing air to enter via filter 16 and heparin vial 16 to atmosphere pressure.

In an embodiment, each of pneumatic valves 70a, 70b, 70c, 70d . . . 70n communicates fluidly with a positive pressure source 72 and a negative pressure source 74. In this manner pneumatic valves 70a, 70b, 70c, 70d . . . 70n can supply positive pressure from source 72 to a fluid valve (e.g., to close the valve) or negative pressure from source 74 to the fluid valve (e.g., to open the valve). Likewise, valves 70a, 70b, 70c, 70d . . . 70n can supply positive pressure from source 72 to a fluid pump (e.g., to pump fluid out of the pump) or negative pressure from source 74 to the fluid pump (e.g., to pull fluid into the fluid pump).

Referring now to FIG. 2, one embodiment of a dialyzer cleaning method operated under the control of control unit 60 is illustrated by method 100. Method 100 begins at oval 102. At block 104 treatment under system 10 ends. The treatment can be any type of blood cleansing treatment, such as hemodialysis ("HD"), hemofiltration ("HF"), hemodiafiltration ("HDF"), and continuous renal replacement therapy ("CRRT"). The end of treatment for system 10 typically involves a blood rinseback to the patient. So that the patient does not lose blood because of the treatment, the blood at the end of treatment is pushed back to the patient. In one embodiment, treatment fluid, such as dialysate, is used to push the blood back through arterial line 22 and venous line 24 to the patient. Alternatively, replacement fluid or saline from source 32 is used to push the blood back through arterial line 22 and venous line 24 to the patient.

At block 106, the patient after blood rinseback disconnects arterial line 22 and venous line 24 from their respective needles and either (i) connects arterial line 22 and venous line 24 together (e.g., using a separate recirculation connector to connect arterial needle connector A to venous needle connector V) or (ii) connects arterial needle connector A to corresponding port A in treatment fluid circuit 40 and venous needle connector V to corresponding port V in treatment fluid circuit 40.

In an embodiment, method 100 transitions automatically from block 106 to block 108 after arterial and venous lines 22 and 24 are connected together or to treatment fluid circuit 40. In an alternative embodiment, method 100 transitions from block 106 to block 108 at the end of treatment and needle disconnection via one or more user input using user the interface (not illustrated) into control unit 60.

At block 108, system 10 causes fluid to be moved back and forth, e.g., vigorously, to remove blood clots, proteins and/or residual biological fluids from the membranes of blood filter 30. In an embodiment, blood pump 28 is used to pulsate treatment fluid, replacement fluid or saline back and forth across the insides of the membranes of blood filter 30. To do so, membrane 28c is sucked and pushed back and forth in time with the sequencing of valves 28a and 28b. If blood pump 28 is a peristaltic pump, the pump rotor is rotated in alternating directions. In an embodiment, blood pump 28 cycles approximately 50 to 300 milliliters ("ml"), e.g., 250 ml, of treatment fluid, replacement fluid or saline back and forth across the insides of the membranes of blood filter 30 approximately twenty times or cycles over a period of about five to twenty, e.g., fifteen, minutes.

Alternatively or additionally, one or both treatment fluid pumps 44 and 50 is used to pulsate treatment fluid, replacement fluid or saline back and forth across the outsides of the membranes of blood filter 30. To do so, the rotors of pumps 44 and 50 are rotated in alternative directions. If pumps 44 and 50 are instead volumetric diaphragm pumps, the associated pump diaphragms and valves are sequenced and cycled as described above for blood pump 28. If treatment pumps 44 and/or 50 is used, treatment fluid pumps 44 and 50 can cycle approximately 50 to 300 ml, e.g., 250 ml, of treatment fluid, replacement fluid or saline back and forth across the outsides of the membranes of blood filter 30, again, approximately twenty times or cycles over a period of about five to twenty, e.g., fifteen, minutes.

Running blood pump 28 in combination with one or both treatment pumps 44 and 50 may desirably balance the pressures on both sides of 30a and 30b of membranes 30c during one or both of the operations discussed in connection with blocks 108 and 110. Or, it may be desirable to maintain a pressure gradient across membranes 30c, e.g., maintaining side 30a at a higher pressure than side 30b. The gradient may be accomplished by running blood pump 28 only, or by running blood pump 28 at a higher pressure than that at which treatment fluid pump 44 and 50 are operated.

In an embodiment, treatment fluid, such as dialysate, already resides in both blood side 30a and treatment fluid side 30b of blood filter 30 from the end of treatment rinseback procedure. It is accordingly logical to use the already present treatment fluid for the pulsating cleansing of block 108. Treatment fluid, such as dialysate, is physiologically safe and tends not to clot or lyse blood in comparison with purified water.

If instead saline resides in one or both of blood side 30a and treatment fluid side 30b of blood filter 30 due to an end of treatment or rinseback procedure, it is logical to use the already present saline for the pulsating cleansing of block 108 (for one or both of blood side 30a and treatment fluid side 30b). Saline is likewise physiologically safe and tends not to clot or lyse blood in comparison with purified water.

If instead replacement fluid resides in one or both of blood side 30a and treatment fluid side 30b of blood filter 30 due to an end of treatment or rinseback procedure, it is logical to use the already present replacement fluid for the pulsating cleansing of block 108 (for one or both of blood side 30a and treatment fluid side 30b). Replacement fluid is likewise physiologically safe and tends not to clot or lyse blood in comparison with purified water.

In alternative embodiments, system 10 pulls treatment fluid, e.g., dialysate or replacement fluid, from a source or storage tank of same. System 10 can pull saline from supply 32, pull replacement fluid from supply 32 or pull dialysate from a holding tank (not illustrated in FIG. 1). The pulled physiologically safe fluid is driven into treatment fluid site 30b of blood filter 30, across membranes 30c, into blood side 30a of blood filter 30 and into blood circuit 20. In an embodiment, about 50 to 300 ml (e.g., 250 ml) of such fluid is pulled and used for the pulsating cleansing of the blood filter membranes of block 108. In any case, because the fluid used to loosen blood clots and proteins from the membrane walls of blood filter 30 is pulsed back and forth and is not sent to drain, no fluid is consumed at block 108.

At block 110, air is injected into blood circuit 20 and blood side 30a of blood filter 30, where it produces an air/treatment fluid (e.g., air/dialysate) mixture. The air/ treatment fluid is pumped in one embodiment so that the mixture enters bottom end 30e of blood filter 30, which may require that the air/treatment fluid mixture first be pumped down the blood filter 30 and then reversed up and out top end 30d of the blood filter 30 depending upon how, as discussed above, blood lines 22 and 24 are connected to blood filter 30. The air treatment mixture can be circulated through the entire blood circuit 20 and/or treatment fluid circuit 40 one or more time. Pumping the treatment fluid up from the bottom 30c of blood filter 30 forces the air through membranes 30c and breaks the air into microbubbles (e.g., effervescence), which helps to remove residual blood, e.g., clots, proteins and biological fluids from blood filter 30. In particular, the effervescent effect is believed to create areas of high shear stresses and turbulence at various air/water interfaces of the surfaces of membranes 30c, which assists in loosening blood residuals.

In an embodiment, air valve 18 is opened and heparin pump 38, including the cycling of fluid valves 38a and 38b (or blood pump 28), is used to pull either air as needed, or a known and desired amount of air, e.g., 25 ml, into blood circuit 20 and blood side 30a of blood filter 30. Here, heparin vial 36 may be empty or removed so that heparin is not injected into the blood lines along with the air. Or, an additional heparin valve (not illustrated) can be provided to isolate heparin vial 36 from the air line. Still further alternatively, heparin entering blood circuit 20 is tolerated. And again, any air entering system 10 via air valve 18 and heparin pump 38 is filtered first via filter 16.

Blood pump 28 is used to pump the air/treatment fluid along filter 30 (e.g., from top to bottom) and throughout blood circuit 20. If connectors A and V of blood lines 22 and 24 are plugged into treatment fluid circuit 40, then blood pump 28 can be used to pump air/treatment fluid through treatment fluid circuit 40 as well. Otherwise, treatment fluid pumps 44 and 50 may be used alternatively or additionally to pump air/treatment fluid through treatment fluid circuit 40. In either case, it is contemplated to alternatively or additionally scrub the outside of membranes 30c of blood filter 30 by passing the air/treatment fluid mixture through to the treatment fluid side 30b of blood filter 30.

Although not illustrated, a second air vent valve 18 and second, e.g., HEPA, filter 16 can be placed in treatment fluid circuit 40. For example, a second air trap 26 can be placed between heater 48 and pump 44 to trap air caused by the heating of the treatment fluid. Second air vent valve 18 and second filter can then be coupled to the upper or air collection portion of air trap 26.

At block 110, it is contemplated for system 10 and control unit 60 to alternatively or additionally pull air into treatment fluid circuit 40 by opening second air valve 18 and operating treatment fluid pump 44 and/or treatment fluid pump 50 to circulate air/treatment fluid into treatment fluid side 30b to scrub the treatment fluid side 30b of blood filter 30 including the outsides of membranes 30c.

Air/treatment fluid may be pulsed back and forth along the insides and/or outsides of the membranes 30c or be flowed around and around form top end 30d to bottom end 30e of blood filter 30 a plurality of times. Air/treatment fluid has a different consistency and shearing effect than does pure liquid, which is believed to provide good particulate loosening in combination with the pure treatment fluid, e.g., dialysate, saline or replacement fluid. It should be appreciated that no dialysate, saline or replacement fluid is sent to drain during the step of block 110, just as with block 108.

At diamond 112, method 100 determines whether the steps at blocks 108 and 110 are to be repeated. If so, method 100 returns to block 108. Here, pure dialysate, saline or replacement fluid may need to be pulled from a source or holding tank to repeat the step of block 108. The operational loop between block 108 and diamond 112 may be repeated any desired number of times. If method 100 determines that the steps at blocks 108 and 110 are not to be repeated, method 100 proceeds to block 114. It is contemplated to use different methodologies for determining when the steps at blocks 108 and 110 are repeated e. The number of repeats can be set in memory as a preset number. The number of repeats can be set as part of a device prescription that is patient specific. The number of repeats can alternatively or additionally be based on other factors, such as one or more of a pressure reading, a bundle volume measurement of the dialyzer, the results of a dialyzer clearance test, the age of the dialyzer (how many uses), for example. It is expressly contemplated therefore that even for the same patient, the number of repeats at diamond 112 may vary from treatment to treatment.

At block 114, air valve 18 is or continues to be opened and heparin pump 38 including the cycling of fluid valves 38a and 38b are used to pull air into blood circuit 20 and blood side 30a of blood filter 30 to purge the blood circuit 20 of all liquid. Again, heparin vial 36 may be empty or removed so that heparin is not injected along with air. Or again, an additional heparin valve (not illustrated) can be provided to isolate heparin vial 36 from the air line. And again, any air entering system 10 via air valve 18 and heparin pump 38 is filtered first via filter 16.

Blood pump 28 can be used to push air/treatment fluid, now loaded with blood residuals, through the filter membranes, into treatment fluid side 30b of blood filter 30, from there into treatment fluid circuit 40, and eventually to drain. If connectors A and V of blood lines 22 and 24 are plugged into treatment fluid circuit 40, then blood pump 28 can be used additionally or alternatively to pump air to push air/treatment fluid, now loaded with blood residuals, directly into treatment fluid circuit 40 and out the drain.

At diamond 116, method 100 determines whether the steps at blocks 108 to 114 are to be repeated. If so, method 100 returns to block 108. Here again, pure dialysate, saline or replacement fluid may need to be pulled from a source or holding tank to repeat the step of block 108. The operational loop between block 108 and diamond 116 may be repeated any desired number of times. If method 100 determines that the steps at blocks 108 to 114 are not to be repeated, method 100 proceeds to block 118.

At block 118, system 10 performs a prime/disinfection procedure to clean the entire system including blood circuit 20 and dialysate circuit 40. Hot water or a chemical solution may be used to prime and disinfect the system. The hot water or chemical solution aids in forcing any remaining blood residuals, e.g., clots or proteins, to drain. The disinfection fluid may be left inside system 10 until the next use or purged again via filtered air so that system 10 is left in a dry condition until the next treatment.

At oval 120, method ends.

As mentioned above, while the present disclosure is described primarily in connection with a blood therapy, e.g., dialysis, machine that reuses the same blood filter 30 over multiple treatments, e.g., around thirty treatments, the concepts discussed herein are not limited to such an application. The apparatus and methodology described herein could be used instead on a dialyzer cleaning machine for example. Here, blood filter 30 is removed from the blood therapy machine after each treatment, brought to the dialyzer cleaning machine, which uses the structure and methodology discussed herein to clean blood filter 30, which is then brought back to the blood therapy machine for reuse.

Also mentioned above, while the present disclosure is described primarily in connection with a blood therapy machine, the present disclosure is equally applicable to a dialysis machine that uses a filter to clean a peritoneal dialysis fluid or ("PD") solution. In such case, the blood circuit 20 described herein is replaced with a peritoneal dialysis fluid circuit that pumps PD solution into and out of the patient's peritoneum and through the insides of the membranes of a PD filter 30. Here, heparin pump 38 and heparin are not needed. Treatment fluid circuit 40 could remain substantially unchanged and pump online or bagged dialysate through PD filter 30 over the outsides of the membranes of the filter to clean the sterile solution returning from the patient's peritoneum.

Additional Aspects of the Present Disclosure

Aspects of the subject matter described herein may be useful alone or in combination with any one or more of the other aspect described herein. Without limiting the foregoing description, in a first aspect of the present disclosure, a method for cleaning a blood filter includes: pumping a physiologically safe fluid back and fourth through the insides and/or the outsides of a plurality of hollow fiber membranes of the blood filter to remove or loosen blood residuals, such as blood clots, proteins and/or biological fluid; injecting air into the physiologically safe fluid to form an air/fluid mixture; pumping the air fluid mixture through the insides and/or outsides of the plurality of the hollow fiber membranes of the blood filter to further or remove or loosen blood residuals therefrom; and removing the air/physiologically safe fluid mixture along with the removed or loosened blood residuals to drain.

In accordance with a second aspect of the present disclosure, which may be used in combination with any other aspect or combination of aspects listed herein, pumping the air/physiologically safe fluid mixture through the insides and/or outsides of the membranes includes breaking the air into microbubbles.

In accordance with a third aspect of the present disclosure, which may be used in combination with any other aspect or combination of aspects listed herein, pumping the air/physiologically safe fluid mixture through the insides and/or outsides of the membranes includes pumping the mixture from a bottom of the blood filter to a top of the blood filter.

In accordance with a forth aspect of the present disclosure, which may be used in combination with any other aspect or combination of aspects listed herein, pumping the air/physiologically safe fluid mixture through the insides and/or outsides of the membranes includes pumping the air/physiologically safe fluid mixture back and forth across the membranes.

In accordance with a fifth aspect of the present disclosure, which may be used in combination with any other aspect or combination of aspects listed herein, pumping the air/physiologically safe fluid mixture through the insides and/or outsides of the membranes includes circulating the air/physiological safe fluid across the membranes a plurality of times.

In accordance with a sixth aspect of the present disclosure, which may be used in combination with any other aspect or combination of aspects listed herein, removing the air/physiologically safe fluid mixture to drain includes injecting air to push the mixture to drain.

In accordance with a seventh aspect of the present disclosure, which may be used in combination with any other aspect or combination of aspects listed herein, the method further includes priming or disinfecting the blood filter after removing the air/physiologically safe fluid mixture to drain.

In accordance with an eighth aspect of the present disclosure, which may be used in combination with any other aspect or combination of aspects listed herein, injecting air includes filtering the air.

In accordance with a ninth aspect of the present disclosure, which may be used in combination with any other aspect or combination of aspects listed herein, injecting air includes pumping air into the blood filter via a blood pump.

In accordance with a tenth aspect of the present disclosure, which may be used in combination with any other aspect or combination of aspects listed herein, pumping the physiologically safe fluid back and forth includes reversing a blood pump.

In accordance with an eleventh aspect of the present disclosure, which may be used in combination with any other aspect or combination of aspects listed herein, pumping the physiologically safe fluid back and forth includes sequencing a plurality of valves.

In accordance with a twelfth aspect of the present disclosure, which may be used in combination with any other aspect or combination of aspects listed herein, the method includes transferring the physiologically safe fluid from outside of the hollow fiber membranes, through walls of the membranes, and into the insides of the membranes to pump the treatment fluid back and forth.

In accordance with a thirteenth aspect of the present disclosure, which may be used in combination with any other aspect or combination of aspects listed herein, the physiologically safe fluid used for pumping back and forth through the insides of the membranes is provided via a rinseback of blood to the patient, leaving physiologically compatible fluid inside of the membranes.

In accordance with a fourteenth aspect of the present disclosure, which may be used in combination with any other aspect or combination of aspects listed herein, the physiologically safe fluid is selected from the group consisting of: dialysate, replacement fluid and saline.

In accordance with a fifteenth aspect of the present disclosure, which may be used in combination with any other aspect or combination of aspects listed herein, the method is used with renal therapy equipment.

In accordance with a sixteenth aspect of the present disclosure, which may be used in combination with any other aspect or combination of aspects listed herein, the blood filter is a dialyzer.

In accordance with a seventeenth aspect of the present disclosure, which may be used in combination with any other aspect or combination of aspects listed herein, a renal therapy system includes: a blood filter including a plurality of hollow fiber membranes; arterial and venous lines in fluid communication with the blood filter; a blood pump for pumping blood through the arterial and venous lines and the blood filter; a treatment fluid pump in fluid communication with (a) a treatment fluid side of the blood filter or (b) the arterial or venous line; and a control unit controlling the blood pump and the treatment fluid pump during treatment and at least one of the blood pump and the treatment pump during a filter cleaning sequence in which (i) a physiologically safe fluid is transferred back and forth across the insides and/or outsides of the plurality of hollow fiber membranes, (ii) the physiologically safe fluid mixed with air is transferred across the insides and/or outsides of the plurality of hollow fiber membranes at least one time, and (iii) the physiologically safe fluid mixed with air and blood residuals loosened or removed from the hollow fiber membranes is transformed to drain.

In accordance with an eighteenth aspect of the present disclosure, which may be used with the seventeenth aspect in combination with any other aspect or combination of aspects listed herein, the system further includes a filtered air access in fluid communication with the blood pump, and a valve, the control unit controlling the valve to selectively allow in the air to be mixed in (ii).

In accordance with a nineteenth aspect of the present disclosure, which may be used with the seventeenth aspect in combination with any other aspect or combination of aspects listed herein, the treatment fluid pump is a replacement fluid pump, the treatment fluid being replacement fluid.

In accordance with a twentieth aspect of the present disclosure, which may be used with the nineteenth aspect in combination with any other aspect or combination of aspects listed herein, the control unit controls the replacement fluid pump to perform at least one of (i), (ii) or (iii).

In accordance with a twenty-first aspect of the present disclosure, which may be used with the seventeenth aspect in combination with any other aspect or combination of aspects listed herein, the treatment fluid pump is a fresh dialysate fluid pump, and wherein the treatment fluid is dialysate.

In accordance with a twenty-second aspect of the present disclosure, which may be used with the seventeenth aspect in combination with any other aspect or combination of aspects listed herein, the system includes a saline supply in fluid communication with the arterial or venous line, the treatment fluid pump being a saline pump, and the physiologically safe fluid being saline.

In accordance with a twenty-third aspect of the present disclosure, which may be used with the seventeenth aspect in combination with any other aspect or combination of aspects listed herein, the control unit is configured to cause the blood pump to perform (i) to (iii) and the treatment fluid pump to be operated during at least one of (i) and (ii) on the outsides of the hollow fiber membranes to attempt to equalize pressures across the hollow fiber membranes.

In accordance with a twenty-fourth aspect of the present disclosure, which may be used with the seventeenth aspect in combination with any other aspect or combination of aspects listed herein, the control unit is configured to cause the blood pump only to perform (i), (ii) and (iii).

In accordance with a twenty-fifth aspect of the present disclosure, which may be used with the seventeenth aspect in combination with any other aspect or combination of aspects listed herein, the control unit is configured to cause the blood pump and the treatment fluid pump to perform (i) and (ii) and the blood pump only to perform (iii).

In accordance with a twenty-sixth aspect of the present disclosure, any of the structure and functionality illustrated and described in connection with FIGS. 1 and 2 may be used in combination with any other aspect or combination of aspects listed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A peritoneal dialysis apparatus comprising:
   a filter including a plurality of hollow fiber membranes;
   a dialysis fluid circuit in fluid communication with the filter;
   a pump for pumping
      fresh dialysis fluid to a peritoneum of a patient via the dialysis fluid circuit, and
      used dialysis fluid from the peritoneum of the patient through the dialysis fluid circuit and the filter;
   a selective air access in fluid communication with the dialysis fluid circuit; and
   a control unit configured to control the pump during a peritoneal dialysis treatment and a filter cleaning sequence in which
      (i) a physiologically safe fluid is transferred across insides and/or outsides of the plurality of hollow fiber membranes at least one time,
      (ii) a fluid mixture is formed by opening the selective air access to mix air with the physiologically safe fluid, and
      (iii) the fluid mixture is transferred across the insides and/or outsides of the plurality of hollow fiber membranes at least one time,
   wherein the filter cleaning sequence is performed such that the fluid mixture is delivered to the filter instead of a drain.

2. The apparatus of claim 1, wherein the physiologically safe fluid includes fresh dialysis fluid.

3. The apparatus of claim 1, wherein the fresh dialysis fluid is (i) prepared from an online source, or (ii) received from a fluid container.

4. The apparatus of claim 1, wherein the pump is configured to pull the air in from outside the selective air access for mixing with the physiologically safe fluid.

5. The apparatus of claim 1, wherein the fluid mixture is configured to enhance loosening or removing residuals from the hollow fiber membranes.

6. The apparatus of claim 1, further comprising an air-passing filter in fluid communication with the selective air access and configured to filter air passing through the selective air access.

7. The apparatus of claim 1, wherein the selective air access is at least one of (a) vented via a protective membrane or (b) selectively accessed via a valve.

8. The apparatus of claim 1, wherein the physiologically safe fluid includes saline provided by a saline supply in fluid communication with the dialysis fluid circuit, and wherein the pump or a second pump is positioned and arranged to pump the saline from the saline supply.

9. The apparatus of claim 1, wherein the control unit is configured to cause the pump to perform at least (i) and (iii) and a second pump to be operated simultaneously in an attempt to equalize pressure across the hollow fiber membranes.

10. The apparatus of claim 1, wherein the control unit is configured to cause the pump to perform at least (i) and (iii), and use a second pump to perform (ii).

11. The apparatus of claim 1, wherein the control unit is configured to cause the pump to perform (ii) and a second pump to perform (i) and (iii).

12. The apparatus of claim 1, wherein the filter is a dialyzer.

13. The apparatus of claim 1, wherein the control unit is configured to cause the physiologically safe fluid to be transferred back and forth across the plurality of hollow fiber membranes a plurality of times before mixing the physiologically safe fluid with the air.

14. The apparatus of claim 1, which is configured to transfer the fluid mixture to the drain after (iii).

15. The apparatus of claim 1, wherein the control unit is configured to perform (iii) such that the fluid mixture is mixed with dialysis fluid instead of being purged to the drain.

16. A method for cleaning a filter during a cleaning sequence, the method comprising:
   (i) pumping a physiologically safe fluid across insides and/or outsides of a plurality of hollow fiber membranes of a filter for peritoneal dialysis;
   (ii) forming a fluid mixture by injecting air into the physiologically safe fluid;
   (iii) during the cleaning sequence, pumping the fluid mixture across the insides and/or outsides of the plurality of hollow fiber membranes of the filter so as to remove or loosen residuals, such as proteins and/or biological fluid,
   wherein the fluid mixture is delivered to the filter instead of a drain during at least (ii) and (iii); and
   (iv) transferring the fluid mixture along with the removed or loosened residuals to the drain,
   wherein the use of the fluid mixture enables the cleaning sequence to be performed after a peritoneal dialysis treatment.

17. The method of claim 16, wherein pumping the fluid mixture across the insides and/or outsides of the plurality of hollow fiber membranes includes at least one of (a) breaking the air into microbubbles, (b) pumping the fluid mixture from a bottom of the filter to a top of the filter, (c) pumping the fluid mixture back and forth across the plurality of hollow fiber membranes, or (d) circulating the fluid mixture across the plurality of hollow fiber membranes a plurality of times.

18. The method of claim 16, wherein the physiologically safe fluid is pumped back and forth across the insides and/or the outsides of the plurality of hollow fiber membranes of the filter so as to remove or loosen the residuals.

19. The method of claim 16, wherein transferring the fluid mixture to the drain includes injecting air to push the fluid mixture along with the removed or loosened residuals to the drain.

20. The method of claim 16, which further includes at least one of:
   priming the filter with at least one of dialysis fluid, replacement fluid, or saline after the transferring performed in (iv); or
   disinfecting the filter with at least one of hot water or a chemical disinfectant after the transferring performed in (iv).

21. The method of claim 16, wherein the cleaning sequence is performed at an end of the peritoneal dialysis treatment when peritoneal dialysis fluid is pumped from a patient's peritoneum.

22. The method of claim 16, wherein injecting the air includes at least one of (a) filtering the air or (b) pumping the air into the filter via a pump.

\* \* \* \* \*